(12) United States Patent
Davis et al.

(10) Patent No.: US 9,107,053 B2
(45) Date of Patent: *Aug. 11, 2015

(54) MESSAGE SERVER

(71) Applicant: Multi-Tech Systems, Inc., Mounds View, MN (US)

(72) Inventors: Jeffrey P. Davis, East Bethel, MN (US); Kevin Sanh Hong, St. Paul, MN (US)

(73) Assignee: Multi-Tech Systems, Inc., Mounds View, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/454,078

(22) Filed: Aug. 7, 2014

(65) Prior Publication Data

US 2015/0065181 A1 Mar. 5, 2015

Related U.S. Application Data

(63) Continuation of application No. 12/239,387, filed on Sep. 26, 2008, now Pat. No. 8,831,674.

(60) Provisional application No. 60/975,580, filed on Sep. 27, 2007.

(51) Int. Cl.
*H04W 4/00* (2009.01)
*H04W 4/14* (2009.01)
(Continued)

(52) U.S. Cl.
CPC ............... *H04W 4/14* (2013.01); *G01K 13/00* (2013.01); *G01N 33/0036* (2013.01); *G08B 25/08* (2013.01); *H04L 12/5835* (2013.01); *H04L 51/066* (2013.01); *H04W 4/12* (2013.01); *H04W 76/007* (2013.01); *H04W 84/042* (2013.01)

(58) Field of Classification Search
CPC ....... H04W 4/14; H04W 4/12; H04W 84/042; H04W 76/007; G08B 25/08; H04L 12/5835; H04L 51/066; G01K 13/00; G01N 33/0036
USPC ............... 455/466, 518, 412.2, 433; 709/246, 709/216, 203, 217
See application file for complete search history.

(56) References Cited

U.S. PATENT DOCUMENTS 6,553,336 B1 * 4/2003 Johnson et al. ............... 702/188
6,580,725 B1 * 6/2003 Phillips et al. ................ 370/461
(Continued)

OTHER PUBLICATIONS

"U.S. Appl. No. 12/136,908, Non Final Office Action mailed Sep. 7, 2011", 15 pgs.
(Continued)

*Primary Examiner* — Mahendra Patel
(74) *Attorney, Agent, or Firm* — Schwegman Lundberg & Woessner, P.A.

(57) ABSTRACT

An apparatus includes a housing, an interface, a processor and a memory. The interface is affixed to the housing and is configured for coupling to a cellular wireless network. The processor is affixed to the housing and is coupled to the interface. The memory is affixed to the housing and is coupled to the processor. The memory is configured to store a set of instructions for causing the processor to receive a first message using the interface and, in response thereto, for causing the processor to broadcast a second message using the cellular wireless network and using the interface, the second message having a transmission parameter determined by the first message and wherein the second message is compatible with a messaging service protocol.

19 Claims, 5 Drawing Sheets

(51) Int. Cl.
*G08B 25/08* (2006.01)
*H04L 12/58* (2006.01)
*H04W 4/12* (2009.01)
*G01K 13/00* (2006.01)
*G01N 33/00* (2006.01)
*H04W 76/00* (2009.01)
*H04W 84/04* (2009.01)

(56) References Cited

U.S. PATENT DOCUMENTS

| | | | |
|---|---|---|---|
| 7,058,036 B1* | 6/2006 | Yu et al. | 370/335 |
| 7,231,403 B1 | 6/2007 | Howitt et al. | |
| 7,778,654 B2 | 8/2010 | Ahn et al. | |
| 2004/0058694 A1 | 3/2004 | Mendiola et al. | |
| 2004/0158428 A1 | 8/2004 | Byrd et al. | |
| 2004/0172222 A1* | 9/2004 | Simpson et al. | 702/189 |
| 2005/0013301 A1* | 1/2005 | Bouchat et al. | 370/395.5 |
| 2006/0014530 A1* | 1/2006 | Denenberg et al. | 455/414.1 |
| 2006/0261940 A1* | 11/2006 | Defant et al. | 340/539.13 |
| 2007/0088488 A1 | 4/2007 | Reeves et al. | |
| 2007/0161380 A1* | 7/2007 | Fok et al. | 455/456.1 |
| 2007/0232275 A1 | 10/2007 | Collins et al. | |
| 2007/0286181 A1 | 12/2007 | Bushmitch et al. | |
| 2008/0209034 A1 | 8/2008 | Shin et al. | |
| 2008/0280562 A1 | 11/2008 | Zebic et al. | |
| 2009/0088192 A1 | 4/2009 | Davis et al. | |
| 2009/0138958 A1 | 5/2009 | Baum et al. | |
| 2009/0315699 A1 | 12/2009 | Satish et al. | |
| 2010/0153853 A1 | 6/2010 | Dawes et al. | |
| 2010/0190515 A1 | 7/2010 | Sharma et al. | |
| 2010/0332821 A1 | 12/2010 | Khalil et al. | |

OTHER PUBLICATIONS

"U.S. Appl. No. 12/239,387, Examiner Interview Summary mailed Mar. 7, 2012", 3 pgs.

"U.S. Appl. No. 12/239,387, Examiner Interview Summary mailed Aug. 10, 2011", 3 pgs.

"U.S. Appl. No. 12/239,387, Final Office Action mailed Dec. 1, 2011", 11 pgs.

"U.S. Appl. No. 12/239,387, Non Final Office Action mailed Mar. 10, 2011", 14 pgs.

"U.S. Appl. No. 12/239,387, Non Final Office Action mailed Oct. 7, 2013", 21 pgs.

"U.S. Appl. No. 12/239,387, Notice of Allowance mailed May 9, 2014", 19 pgs.

"U.S. Appl. No. 12/239,387, Response filed Mar. 1, 2012 to Final Office Action mailed Dec. 1, 2011", 8 pgs.

"U.S. Appl. No. 12/239,387, Response filed Apr. 2, 2014 to Non Final Office Action mailed Oct. 7, 2013", 12 pgs.

"U.S. Appl. No. 12/239,387, Response filed Aug. 10, 2011 to Non Final Office Action mailed Mar. 10, 2011", 8 pgs.

* cited by examiner

MESSAGE SERVER

CLAIM OF PRIORITY

This application is a continuation under 35 U.S.C. §120 of U.S. patent application Ser. No. 12/239,387, filed on Sep. 26, 2008, and claims the benefit of priority, under 35 U.S.C. §119(e), to U.S. Provisional Patent Application Ser. No. 60/975,580, filed on Sep. 27, 2007. U.S. patent application Ser. No. 12/239,387 and U.S. Provisional Patent Application Ser. No. 60/975,580 are incorporated herein by reference.

TECHNICAL FIELD

This document pertains generally to communications, and more particularly, but not by way of limitation, to a message server.

BACKGROUND

Many types of cellular telephones or other portable devices are able to communicate message using a particular type of protocol referred to as short message service, or SMS. The technology available for establishing and supporting an SMS system is inadequate.

OVERVIEW

An example of the present subject matter includes a device having a housing which includes hardware and instructions to communicate a message in a protocol compatible with SMS or other messaging service. An externally accessible connector allows the device to be linked to a network and configured for operation. In one example, the device can be coupled to a computer that can be used for configuring, monitoring, and managing of the device. The device communicates using a cellular network connection.

In some examples, the device is referred to as a server, however, in other instances, the device can be implemented as a gateway.

This overview is intended to provide an overview of subject matter of the present patent application. It is not intended to provide an exclusive or exhaustive explanation of the invention. The detailed description is included to provide further information about the present subject matter.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Messaging Services—Introduction

Figure 1:
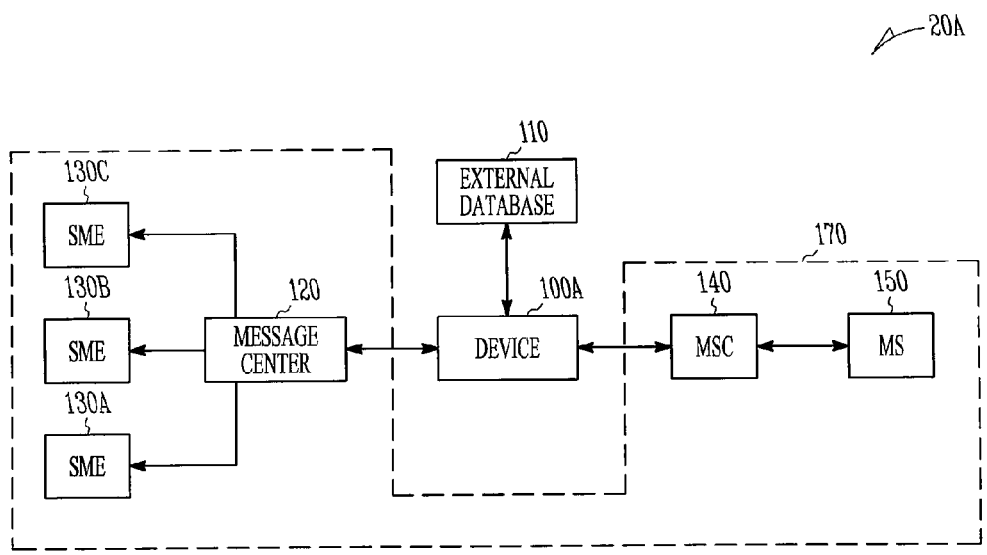
FIG. 1 illustrates selected components of a message communication system according to one example.

Short Message Service (SMS) supports the transfer of messages between a mobile station using a Global System for Mobile communications (GSM) in a public land mobile network (PLMN) and a short message entity via a Service Center, as described in TS GSM 03.40. In SMS, the terms "MO" (Mobile Originating) and "MT" (Mobile Terminating) indicate the direction in which the short message is sent.

The SMS structure uses a system of control messages having elements described as a protocol discriminator, transaction identifier, message type, and information elements. An SMS message is generally recognized as having a length of 160 characters, however, other lengths are contemplated.

In addition to GSM, SMS can be compatible with mobile standards such as American National Standards Institute (ANSI) code division multiple access (CDMA) networks, Advanced Mobile Phone System (AMPS), satellite and landline networks, 3G (third generation of wireless technology), Wi-Fi (wireless fidelity), and WiMAX (Worldwide Interoperability for Microwave Access). An SMS message can be a mobile-to-mobile text message or it can be a type of broadcast message sent over a mobile network.

An SMS message is communicated using a Service Center which acts as a store and forward center for short messages. The Service Center communicates with the Public Land Mobile Network (PLMN) or public switched telephone network (PSTN) via Interworking and Gateway MSCs. An SMS message can include alphanumeric characters and can include various languages such as English, Chinese, Arabic, Japanese, and Korean.

Subscriber originated messages are transported from a handset to a Service Center, and may be destined for mobile users, subscribers on a fixed network, or Value-Added Service Providers (VASPs) also known as application terminated. Subscriber terminated messages are transported from the Service Center to the destination handset, and may originate from mobile users, from fixed network subscribers, or from other sources such as VASPs.

The Short Message Service is supported on most digital mobile phones and some personal digital assistants with on board wireless telecommunications. Text enabled fixed-line handsets are required to receive messages in text format, however messages can be delivered to non-enabled phones using text-to-speech conversion.

When transmitted, an SMS message is sent to a Short Message Service Center (SMSC) which provides a store-and-forward mechanism. It attempts to send messages to their recipients. If a recipient is not reachable, the SMSC queues the message for later retry. Some SMSCs also provide a "forward and forget" option where transmission is tried only once. Both Mobile Terminated (MT), for messages sent to a mobile handset, and Mobile Originating (MO), for those that are sent from the mobile handset, operations are supported. Message delivery is best effort, so there are no guarantees that a message will actually be delivered to its recipient and delay or complete loss of a message is not uncommon, particularly when sending between networks. Users may choose to request delivery reports, which can provide positive confirmation that the message has reached the intended recipient.

Larger messages can be sent segmented over multiple SMS messages, in which case each message will start with a user data header (UDH) containing segmentation information.

Short messages can also be used to send binary content such as ringtones or logos, as well as Over-the-Air programming (OTA) or configuration data. Such uses are a vendor-specific extension of the GSM specification and there are multiple standards.

The SMS specification includes a definition for an external Terminal Equipment, such as a PC or Pocket PC, to control the SMS functions of a mobile phone. The connection between the Terminal Equipment and the mobile phone can be realized with a serial cable, a Bluetooth link, an infrared link, etc. The interface protocol is based on AT commands.

SMS can also be used for machine to machine communication. For example, a machine can be remotely controlled by SMS. In addition, vehicle tracking can be conducted using SMS for data transport or telemetry.

Mobile terminated short messages can be used to deliver digital content such as news alerts, financial information, logos and ring tones. The VASP providing the content submits the message to the mobile operator's SMSC(s) using a TCP/IP protocol such as the Short message peer-to-peer protocol (SMPP) or the External Machine Interface (EMI). The SMSC delivers the text using the normal Mobile Terminated delivery procedure.

Mobile originated short messages can also be used for services such as televoting. In this case, the VASP providing the service obtains a Short Code from the telephone network operator, and subscribers send texts to that number.

In telecommunication, a public land mobile network (PLMN) is a network that is established and operated by an administration or by a recognized operating agency (ROA) for the specific purpose of providing land mobile telecommunications services to the public.

Access to PLMN services is achieved by means of an air interface involving radio communications between mobile phones or other wireless enabled user equipment and land based radio transmitters or radio base stations.

A public land mobile network (PLMN) is any wireless communications system intended for use by terrestrial subscribers in vehicles or on foot. Such a system can stand alone, but often it is interconnected with a fixed system such as the public switched telephone network (PSTN). An example of a PLMN end user is a person with a cell phone.

Certain of the examples discussed in this document refer to a specific messaging services. However, it will be understood that, in addition to short messaging service (SMS), the present subject matter can be used with Instant Messaging (IM), EMS (Enhanced Messaging Service), MMS (Multimedia Messaging Service) as well as other such services. These and other messaging systems can be installed and configured for operation as described herein.

Hardware

FIG. 1 illustrates selected components of a message communication system 20A. In system 20A, device 100A is coupled to an external database 110 and to communication network 170. Device 100A can be described as a gateway or as a server configured for message communication. In one example, device 100A is an SMS server.

Device 100A receives and sends messages in a communication protocol compatible with, for example, SMS, IM, EMS, MMS or other protocols. Device 100A provides an interface between different communication networks. In one example, a message received from mobile station 150, via communication network 170 causes device 100A to determine addressing information for mobile station 150 based on data stored at the mobile switching center 140. In one example, message center 120 provides addressing information for a short messaging entity (SME), examples of which are shown at 130A, 130B, and 130C.

Mobile switching center 140 includes a database for the mobile elements of the communication network 170. Database contents include profile and routing information for each SME. In addition, mobile switching center 140 provides switching connections between mobile stations and the communication network. In one example, mobile switching center 140 manages routing of information between the elements of communication network 170.

In various examples, a first message from mobile station 150 can be sent, via the mobile switching center 140, to device 100A. The first message can be compatible with SMS and can include selected parameters for use by device 100A in generating and routing particular messages to selected entities in communication with message center 120. Each of short message entities 130A, 130B, and 130C can include, in various examples, a cellular telephone, a personal digital assistant (PDA), a portable computer, or other communication device. In various examples, mobile station 150 can include a cellular telephone, a PDA, a portable computer, or other communication device.

Communication network 170 can include a cellular communication network (such as a Wi-Fi network) and, in various examples, includes a PLMN. In one example, communication network 170 includes a wireless communication network that provides coverage for a specific location or geographical area.

Figure 2:
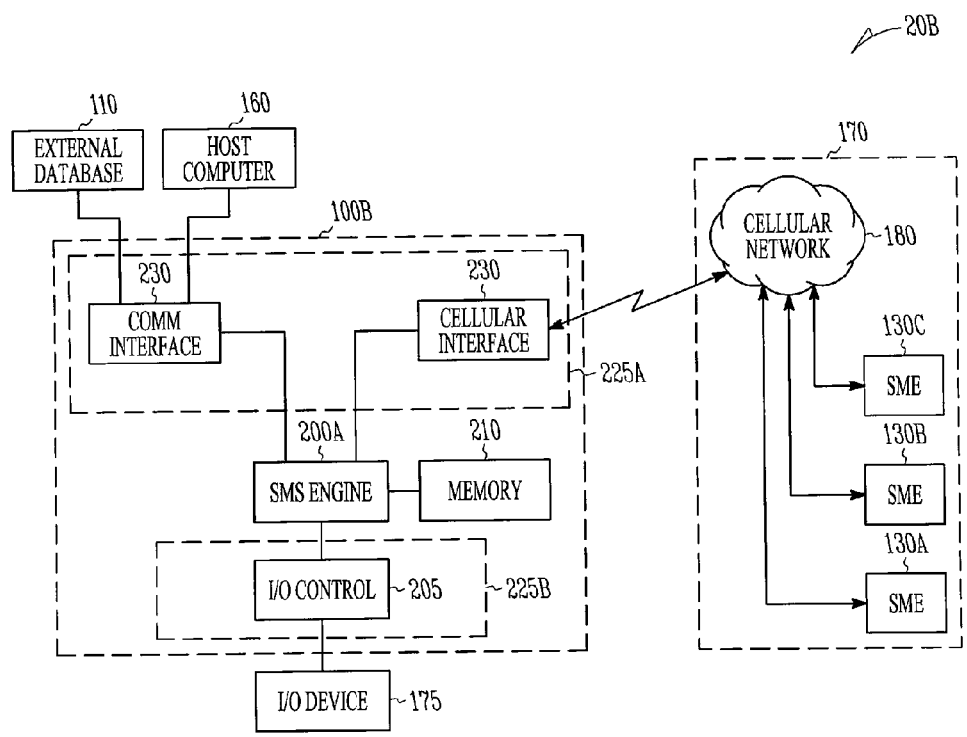
FIG. 2 illustrates a block diagram of a device according to one example.

FIG. 2 includes a block diagram of communication system 20B having device 100B. Device 100B is shown coupled to external database 110 and to communication network 170. Communication network 170 includes cellular network 180 which allows communicating with SME 130A, SME 130B, and SME 130C.

Device 100B includes processor 200A coupled to network interface 225, and memory 210. Processor 200A (sometimes called an engine or SMS engine) executes instructions to implement an algorithm stored in memory 210. Memory 210, in various examples, also includes storage for an internal address book or other internal database. The contents of memory 210 can include a database of subscribers to the particular SMS service and, in one example these addresses represent telephone numbers (or e-mail addresses) to which short messages are to be broadcast or from which messages have been received.

Network interface 225 is illustrated as a first portion 225A (including communication interface 230 and cellular interface 220), and as a second portion 225B (including I/O control 205). Network interface 225 enables communication with devices and networks external to device 100B. In one example, device 100B is contained within a housing and external wired connections are via connectors and external wireless connections are via an antenna.

Communication interface 230 is coupled to external database 110 or host computer 160 by a wired connection (as shown in the figure) or by a wireless connection. Examples of a wired connection for communication interface 230 can include an Ethernet connection, an RS-232 interface, or other such wired interface. Examples of a wireless connection for communication interface 230 can include Wi-Fi, Bluetooth, ZigBee, WiMAX, or other wireless protocol. In addition, external database 110, in various examples, is connected via a network connection which can include a wired connection (such as an Ethernet network) or a wireless connection. Cellular interface 220 is in bi-directional communication with communication network 170 by way of a cellular interface or modem which can include any combination of wired or wireless links. In various examples, cellular interface 220 includes a cellular modem, a multi-port cellular modem (such as a 4-port modem, an 8-port modem) or other such device. The number of ports refers to the number of radios and, thus, the number of simultaneous transmissions (or messages) that can be sent simultaneously.

Input/Output control 205 provides a generic interface to allow external communications with device 100B using I/O device 175. In one example, I/O device 175 communicates with processor 200A using I/O control 205. I/O device 175 can include a sensor, a visual display, a computer (such as a host computer), or other device. Other examples for I/O device 175 can include a serial port device, an alarm device, a programmable logic controller (PLC), a key telephone system, a relay, a temperature sensor, a general purpose input/output (GPIO), or other device to receive or generate signals that can include analog or digital data. In one example, I/O device 175 includes a communication network such as a local area network (LAN) or a wide area network (WAN, such as an internet).

Figure 3:
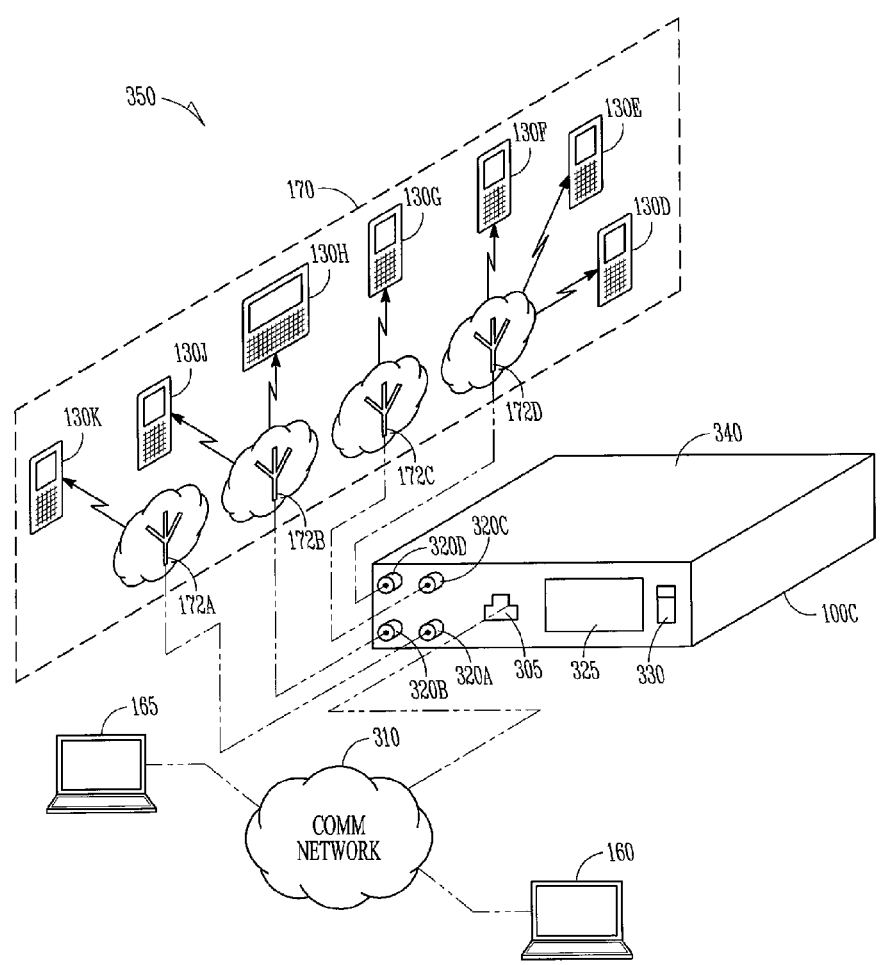
FIG. 3 illustrates a device configured for message communication according to one example.

FIG. 3 illustrates system 350 including device 100C coupled to communication network 170 and communication network 310. System 350 can be located and installed, for example, at a school or commercial facility to allow broadcast communication of short messages with subscribers carrying mobile devices. In the figure, the mobile devices are denoted here as short message entities 130D, 130E, 130F, 130G, and 130H, and, in the context of a school application, each can be viewed as representing teachers, students or parents.

Device 100C includes housing 340. In various examples, housing 340 is fabricated of such materials as plastic or metal. In some examples, housing 340 has features to allow rack mounting or features to allow installation within an expansion slot of a computer.

In the example illustrated, external features affixed to housing 340 include power switch 330, display 325, connector 305 and connectors 320A, 320B, 320C, 320D. Display 325, as shown in the particular example illustrated, can provide visual information concerning functionality, performance or other parameters as to operation of device 100C and tailored for the benefit of an operator. Connector 305 provides a link (such as a wireless or wired electrical connection) to communication network 310.

Communication network 310 includes host computer 160 and networked computer 165, either of which can enjoy management or monitoring rights over device 100C. Communication network 310 can be a LAN or a WAN as well as wired or wireless. In one example, communication network 310 includes a global system of interconnected computer networks that interchange data by packet switching, one example of which includes the internet. Computers 160 and 165 can be local or remote relative to the location of device 100C. In one example, connector 305 includes a CAT-5 connector for use with an Ethernet. In various examples, connector 305 provides a link to at least one of I/O control 205, communication interface 230, and cellular interface 220. In one example, connector 305 is omitted and a wireless interface provides a connection between communication network 310 and device 340. An example of a wireless interface includes a Bluetooth radio.

Connectors 320A, 320B, 320C, and 320D, in one example, are coupled to cellular interface 220 within housing 340. Connectors 320A, 320B, 320C, and 320D, allow connection to a number of antennas or other device to provide access to a cellular communication network or to a PLMN. In FIG. 3, connector 320A, 320B, 320C, and 320D are coupled to antennas 172A, 172B, 172C, and 172D, respectively. The connections (e.g., between connector 320A and antenna 172A) can be wired or wireless as denoted by the dashed lines used in the figure. Antennas 172A, 172B, 172C, and 172D, communicate with mobile devices using corresponding wireless networks, denoted herein by a cloud about each antenna. The example illustrated includes a four-channel device having four radios, each corresponding to a connector and coupled to an antenna. In other examples, the present subject matter includes a single-port device or an eight-port device where the number of ports corresponds to the number of radios. Numbers of ports other than one, four, and eight are also contemplated.

In various examples, communication network 170 includes a large number of subscribers, each of which communicates using various mobile devices.

Methods

Various methods are implemented by different examples of the present subject matter. In some examples, an algorithm executed by a processor is configured to implement a communication, diagnostic, configuration or other function as described herein. In some examples, an algorithm is stored as executable code or instructions for use by a processor or a computer.

Figure 4:
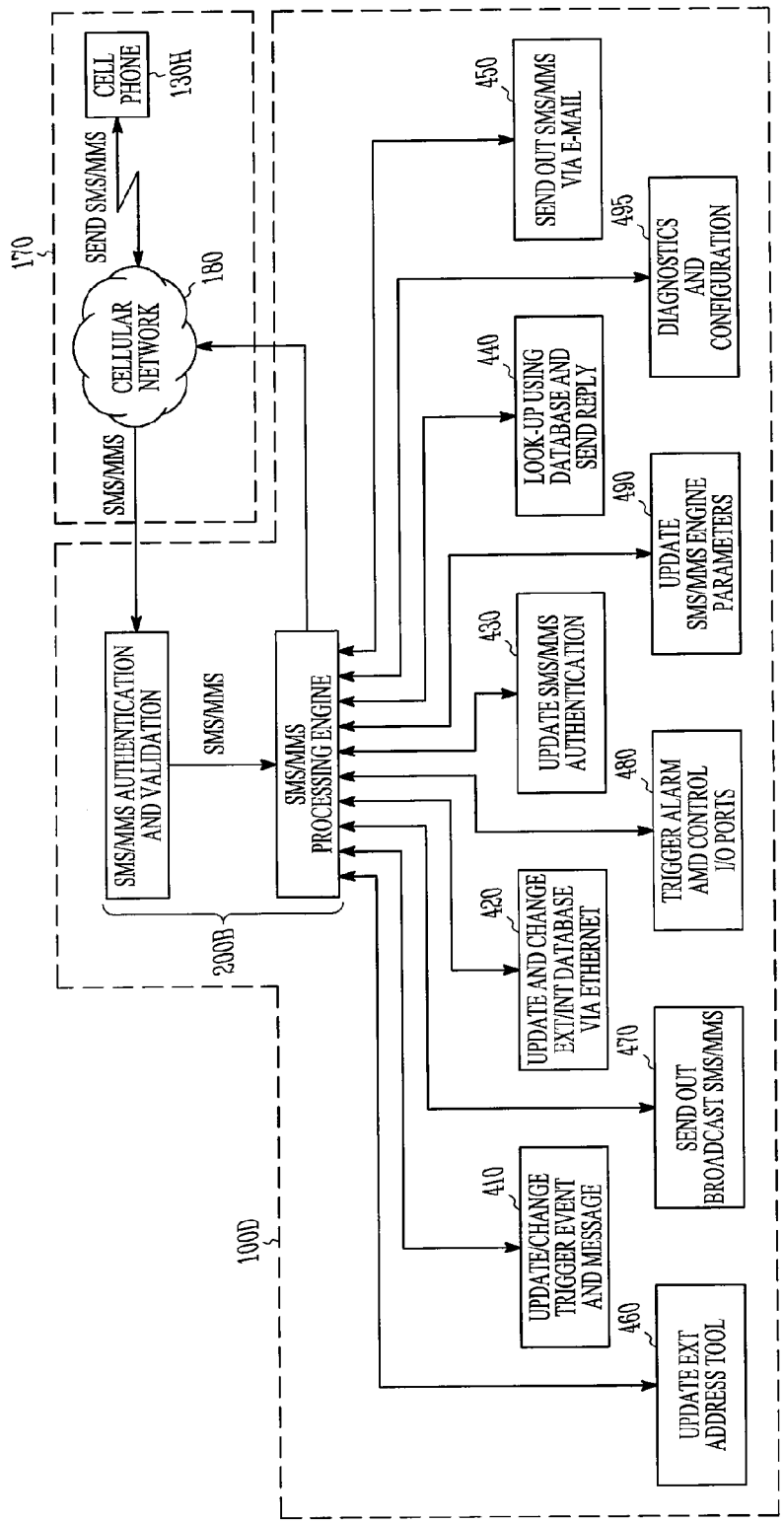
FIG. 4 illustrates selected functionality of a system according to one example.

FIG. 4 illustrates a number of examples of functions that can be implemented. FIG. 4 illustrates a portion of device 100D, namely processor 200B, configured to perform selected functions. Processor 200B is shown in the figure to include an authentication and validation layer and a processing engine layer, however, other layers or structures are also contemplated. A number of modules are illustrated and their functions described in association with FIG. 4, however, in any particular example of the present subject matter, different such modules and functions may be used.

In the figure, short message entity 130H (here illustrated as a cellular telephone) is depicted as sending a message in a protocol compatible with SMS or MMS. The message is illustrated within the boundaries of communication network 170, and as such, can be propagated independent of device 100D. Cellular network 180 then forwards the message to processor 200B.

At 410, device 100D provides services to update and change a trigger event and to update and change a message destined for broadcasting. A trigger event can include, for example detection of an elevated temperature or presence of smoke, either of which could indicate that a fire is burning. In one example, a trigger event is detected by I/O device 175 (FIG. 2). Module 410 can also update and change the message to denote the address of a burning building or to trigger an audible alarm at the particular building. Module 410 can also change a message from, for example, notification of inclement weather, to notification of a power outage. In one example, detection (or receipt of) a signal based on a trigger event can be used to broadcast one or more outbound SMS messages. At 420, device 100D provides services to update and change the contents of an external database 110 or internal memory 210, using, for example, an Ethernet network connection. At 430, device 100D provides services to an change an SMS/MMS authentication code. For example, a received SMS message can invoke a change in an authentication routine or change a value of a parameter used in an authentication routine. At 440, device 100D provides services to look up selected data from a database (such as external database 110 or internal memory 210) and send a reply. At 450, device 100D provides services to send out, or broadcast, an SMS/MMS message via e-mail. At 460, device 100D provides services to update the contents of external database 110 or memory 210, any of which can provide storage for an address book. At 470, device 100D provides services to broadcast an SMS/MMS message. In various examples, the message is broadcast in response to detecting a trigger event or receiving a trigger signal. At 480, device 100D provides services to trigger alarm and control I/O ports. The function represented by module 480 can be performed, in part, by I/O device 175. For example, I/O device 175 along with module 480 can be configured to operate a door, activate an alarm, read data on a port, or otherwise control a device. In addition, I/O device 175 can be used to detect a trigger event and provide a signal to launch an outbound message. At 490, device 100D provides services to update an SMS/MMS engine parameter, an example of which includes changing a keyword. At 495, device 100D provides services to diagnose or configure a system. In various examples, module 495 can provide diagnostic services to determine a condition as to the device, a network, a memory, a sensor, a wireless connection, and a wired connection. In various examples, module 495 can be configured to read a memory or perform a diagnostic routine. Module 495 can be configured to provide a result as to reading the memory or performing the diagnostic routine. The results of the diagnostic routine can be conveyed, for example, using an SMS message or an e-mail message.

In the figure, modules 410, 420, 430, 440, 450, 460, 470, 480, 490, and 495 are shown linked with processor 200B by a bidirectional link. The bidirectional link indicates that each module is in communication with processor 200B and certain data is exchanged as part of the function performed by each module. In addition, a directional arrow in the figure represents the link between cellular network 180 and processor 200B to denote an authentication and validation routine performed on an incoming message. Outgoing messages from device 100D are also represented in the figure by a directional arrow from processor 200B to cellular network 180.

The present subject matter can be configured to implement a variety of applications. For example, a pizza delivery service may configure a device to distribute coupons or an elementary school may configure a device to alert parents, students, or teachers as to schedule changes. The messages in these examples can be configured or triggered for delivery by an administrator using a remote client such as, for example, a browser, a remote SMS device, a mobile station, or other such device.

Figure 5:
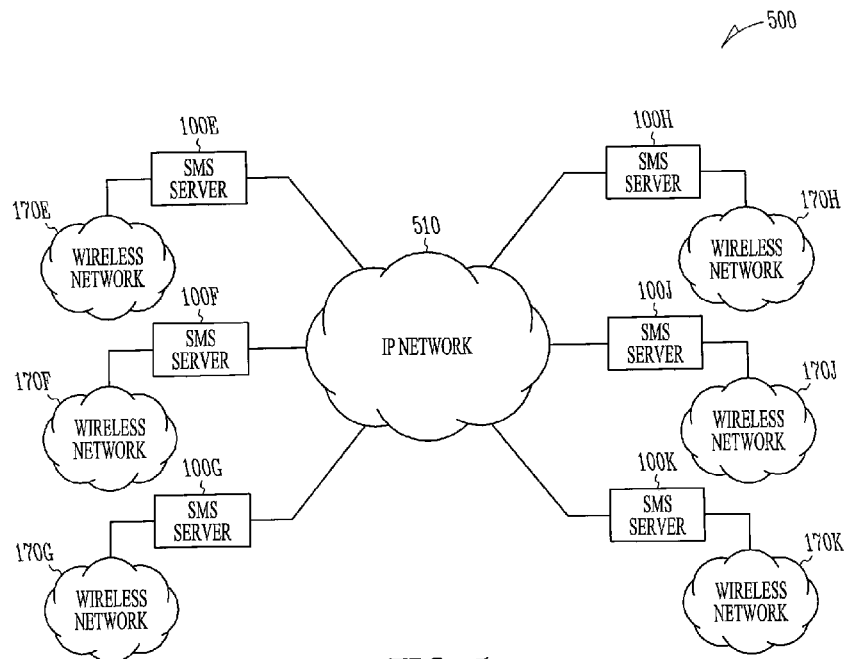
FIG. 5 illustrates a system according to one example.

FIG. 5 illustrates system 500 having devices 100E, 100F, 100G, 100H, 100J, and 100K interconnected by network 510. Network 510 can include an IP protocol communication network and in the example shown, can include the internet. Devices 100E, 100F, 100G, 100H, 100J, and 100K, in the example shown, are each labeled to denote an SMS server, however each can also be referred to as an SMS finder.

System 500 can illustrate a load balancing or master-slave relationship. Consider an example in which devices 100E, 100F, 100G, 100H, 100J, and 100K, are distributed over a large geographic region. For example, devices 100E, 100F, and 100G can be located in San Jose, Chicago, and New York, respectively, and devices 100H, 100J, and 100K can be located in the UK, India, and China, respectively. Each of devices 100E, 100F, 100G, 100H, 100J, and 100K, are in communication with a wireless network 170E, 170F, 170G, 170H, 170J, and 170K, respectively.

In accordance with this example, a handheld device, in communication with device 100E (in San Jose) can send an SMS message, via network 510 and via device 100H (in the UK), to a handheld device in communication with wireless network 170H.

An example of system 500 can be configured to allow a selected device to operate as a master device in order to communicate with one or more slave devices. By operating in a master-slave relationship, system 500 can provide load balancing and improved distribution among a number of system elements. The master device (assume, for example, device 100E) will query the other devices (also coupled to network 510) to determine their identity and to determine their available bandwidth in order to accommodate additional message operations. After checking the load status of the slave devices (in this example, devices 100F, 100G, 100H, 100J, and 100K), the master device will distribute the message to the various devices using network 510. In this example, device 100H, for example, will send the SMS message wirelessly using wireless network 170H. System 500 allows polling of the slave devices and load balancing to achieve uniform distribution of a load.

In one example, devices 100H, 100J, and 100K are in close proximity and wireless networks 170A, 170B, and 170C are in correspondingly close (or overlapping) proximity.

Figure 6:
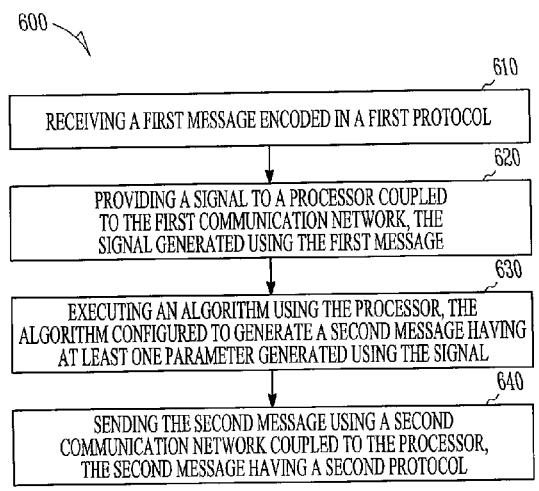
FIG. 6 illustrates a method according to one example.

In one example, the present subject matter includes method 600 as illustrated in FIG. 6. At 610, method 600 includes receiving a first message encoded in a first protocol. The first message is received using a first communication network. Receiving the first message can include receiving a wireless message from a cellular device. Receiving the first message can include receiving using a wired connection. Receiving the first message can include receiving a message having an instruction to read a memory or to perform a diagnostic routine.

At 620, method 600 includes providing a signal to a processor coupled to the first communication network. The signal is generated using the first message.

At 630, method 600 includes executing an algorithm using the processor. The algorithm is stored in a memory coupled to the processor. The memory and the processor are enclosed in a housing. The housing includes an interface to the first communication network. The algorithm is configured to generate a second message having at least one parameter generated using the signal.

At 640, method 600 includes sending the second message using a second communication network coupled to the processor. The second message has a second protocol. The housing includes an interface to the second communication network and the second protocol includes a messaging service. The second message can be sent in response to receiving a trigger signal from a trigger device coupled to the processor.

Method 600 can include exchanging data with a host computer to control the algorithm executed by the processor.

The first communication network can include the second communication network.

In one example, the algorithm is configured to read the memory or perform a diagnostic routine and in one example, the second message includes a result obtained from execution of the algorithm. In one example, the algorithm is configured to determine a available capacity of a device coupled to the first communication network.

Additional Examples

In one example, all communications with the device are conducted using the cellular network. For example, a remote subscriber can craft a message and send the message to the device by entering a particular telephone number. In one example, upon establishing a connection (the connection can include an SMS message or it can include messaging over an IP network), the subscriber then communicates a coded message to the device. In response to receiving the coded message, the device then generates an outgoing message for broadcast delivery to selected SMEs. Addressing information and message information is delivered to the device by means of an incoming call from an authorized SME or subscriber. In this example, the addressing information (telephone numbers) are stored internally in a directory. As such, connector 320 provides both transmit and receive capabilities.

An outgoing message can be broadcast in response to receiving a trigger signal or in response to detecting a trigger event. In various examples, the incoming message, outgoing message, or the trigger signal are received or transmitted using a communication protocol such as File Transfer Protocol (FTP) or TELNET.

In various examples, connector 305 allows a connection to interface with a host personal computer or a network (such as a LAN).

In various examples, a telephone directory is stored internally or externally.

Device 100C can be operated in a stand-alone mode, that is, without connection to a host computer. In other examples, device 100C uses processing services from a host computer.

In various examples, certain of the system elements described herein are located within a housing. For example, the processor, interface, and memory can be located inside of a housing and externally mounted connectors allow electrical connection to internal elements.

In one example, a first message received from an authorized SME (or host processor, or other source) is used to generate a second message for broadcast transmission. For example, a parameter in the first message may provide details as to those addressees that are to receive the second message, or the parameter can relate to the content of the second message that is transmitted.

In various examples, the device includes an interface configured for communicating in a wireless protocol that is compatible with at least one of global system for mobile communications (GSM), code division multiple access (CDMA), advanced mobile phone system (AMPS), a satellite network, a landline network, third generation of wireless technology (3G), wireless fidelity (Wi-Fi), and worldwide interoperability for microwave access (WiMAX).

In various examples, a message for delivery using the present subject matter can be configured using a computer coupled to a network and executing a browser. In addition, a browser-based application can be used to establish and manage a distribution list (including address information or telephone numbers). Furthermore, the delivery of a broadcast message can be triggered using a SME using a wired or wireless communication network. In some examples, the SME that sent the first message receives notification upon broadcasting or sending the second message.

In one example, a device of the present subject matter is configured to query a database based on a subscriber request (received in a first message) in order to generate or distribute a second message.

Additional Notes

The above detailed description includes references to the accompanying drawings, which form a part of the detailed description. The drawings show, by way of illustration, specific embodiments in which the invention can be practiced. These embodiments are also referred to herein as "examples." All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, the code may be tangibly stored on one or more volatile or non-volatile computer-readable media during execution or at other times. These computer-readable media may include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

What is claimed is:

1. A system comprising:
   a processor having an interface for coupling with a cellular wireless network; and
   a memory coupled to the processor and having instructions stored therein for executing an algorithm, the algorithm configured to receive a first message from an I/O device, the interface configured to communicate with the I/O device, the first message having a first message protocol and configured to trigger the algorithm to monitor for and detect a predetermined condition corresponding to a trigger event associated with an alert from the I/O device, the I/O device including a sensor, and after having detected the predetermined condition, configured to send a second message using the interface and using the cellular wireless network, the second message having a second message protocol different than the first message protocol, and wherein the second message includes content determined by the trigger event of the first message and the content of the second message comprising an event type and an event location.

2. The system of claim 1 wherein the I/O device includes at least one of a serial port device, an alarm device, a programmable logic controller (PLC), a key telephone system, a relay, a temperature sensor, a general purpose input/output (GPIO), or a device to receive or generate a signal that can include analog or digital data.

3. The system of claim 1 wherein the predetermined condition includes an elevated temperature or presence of smoke.

4. The system of claim 1 wherein the second message includes a building address.

5. The system of claim 1 wherein the second message includes a notification of weather.

6. The system of claim 1 further including receiving a third message, the third message encoded in the second message protocol, the third message configured to request the processor to execute a diagnostic routine.

7. The system of claim 1 wherein the second message protocol includes a short message service (SMS) message.

8. The system of claim 1 wherein the processor is configured to broadcast the second message using a network of mobile devices.

9. The system of claim 1 wherein the interface is in communication with a mobile switching center.

10. A method performing at a communication device, further comprising:
receiving a first message from an I/O device, the first message received using a processor coupled to an interface, the interface configured to communicate with the I/O device, the first message sent in response to detecting a predetermined condition corresponding to a trigger event associated with an alert from the I/O device, the I/O device including a sensor, the first message having a first message protocol; and
after receiving the first message, sending a wireless message using the interface, the interface coupled to a cellular wireless network, the wireless message having a second message protocol different from the first message protocol, and wherein the wireless message includes content determined by the trigger event of the first message and the content of the wireless message comprising an event type and an event location.

11. The method of claim 10 wherein receiving the first message from the I/O device includes receiving the first message from at least one of a serial port device, an alarm device, a programmable logic controller (PLC), a key telephone system, a relay, a temperature sensor, a general purpose input/output (GPIO), or a device to receive or generate a signal that can include analog or digital data.

12. The method of claim 10 wherein receiving the first message from the I/O device includes detecting an elevated temperature or presence of smoke using the I/O device.

13. The method of claim 10 wherein sending the wireless message includes sending a building address.

14. The method of claim 10 wherein sending the wireless message includes sending a notification of weather.

15. The method of claim 10 further including receiving a third message, the third message encoded in the second message protocol, the third message configured to request the processor to execute a diagnostic routine.

16. The method of claim 10 wherein sending the wireless message includes sending a short message service (SMS) message.

17. The method of claim 10 wherein sending the wireless message includes broadcasting the wireless message using a network of mobile devices.

18. The method of claim 10 wherein sending the wireless message includes communicating with a mobile switching center.

19. The method of claim 10 wherein sending the wireless message includes transferring a message between a mobile station and a short message entity, the message comprising digital content, a news alert, financial information, or multimedia content.

* * * * *